United States Patent [19]

Alexander

[11] Patent Number: 5,334,186
[45] Date of Patent: Aug. 2, 1994

[54] MEDICAL TUBING AND IMPLEMENT ORGANIZER

[76] Inventor: Stephen M. Alexander, 2926 Wenwood, Abilene, Tex. 79606

[21] Appl. No.: 973,724

[22] Filed: Nov. 9, 1992

[51] Int. Cl.⁵ .............................................. A61M 5/32
[52] U.S. Cl. ..................... 604/180; 604/174; 604/177; 604/178; 604/179; 128/DIG. 26; 128/DIG. 15; 5/503.1; 5/658; 248/68.1; 248/205.2
[58] Field of Search ............... 128/DIG. 26, DIG. 15; 604/174, 177–180; 433/93; 269/16; 5/503.1, 507.1, 658, 922; 248/68.1, 74.4, 205.2

[56] References Cited

U.S. PATENT DOCUMENTS

| | | |
|---|---|---|
| 3,696,920 | 10/1972 | Lahay . |
| 4,416,664 | 11/1983 | Womack ............................ 604/174 |
| 4,417,710 | 11/1983 | Adair . |
| 4,606,735 | 8/1986 | Wilder et al. . |
| 4,720,881 | 1/1988 | Meyers ................................ 5/503.1 |
| 4,775,121 | 10/1988 | Carty ................................... 248/68.1 |
| 4,795,429 | 1/1989 | Feldstein ............................ 604/174 |
| 4,795,441 | 1/1989 | Bhatt . |
| 4,955,864 | 9/1990 | Hajduch .................... 128/DIG. 26 |
| 5,102,399 | 4/1992 | Chu . |
| 5,167,630 | 12/1992 | Paul .................................... 604/174 |
| 5,224,674 | 7/1993 | Simons ............................... 248/68.1 |
| 5,226,892 | 7/1993 | Boswell .............................. 604/180 |

Primary Examiner—Randall L. Green
Assistant Examiner—P. Zuttarelli
Attorney, Agent, or Firm—Richard C. Litman

[57] ABSTRACT

A medical implement and tubing organizer that allows medical implements to be held in a convenient location proximate to a patient and also allows the medical tubes to be organized and ordered according to size. The tubes are held in generally cylindrical lateral bores in the tubing holder. The holder is in detachable engagement with a substantially flat base portion. The base portion has a plurality of apertures adapted to receive and hold medical implements. The flat base portion also has a strap or the like to engage the rail or horizontal strut of a hospital bed. Thus, the entire unit is held in a fixed relationship with the patient for the convenience of the caregiver and the tube holding portion can be removed from the base, if desired, to facilitate turning or relocating the patient.

14 Claims, 2 Drawing Sheets

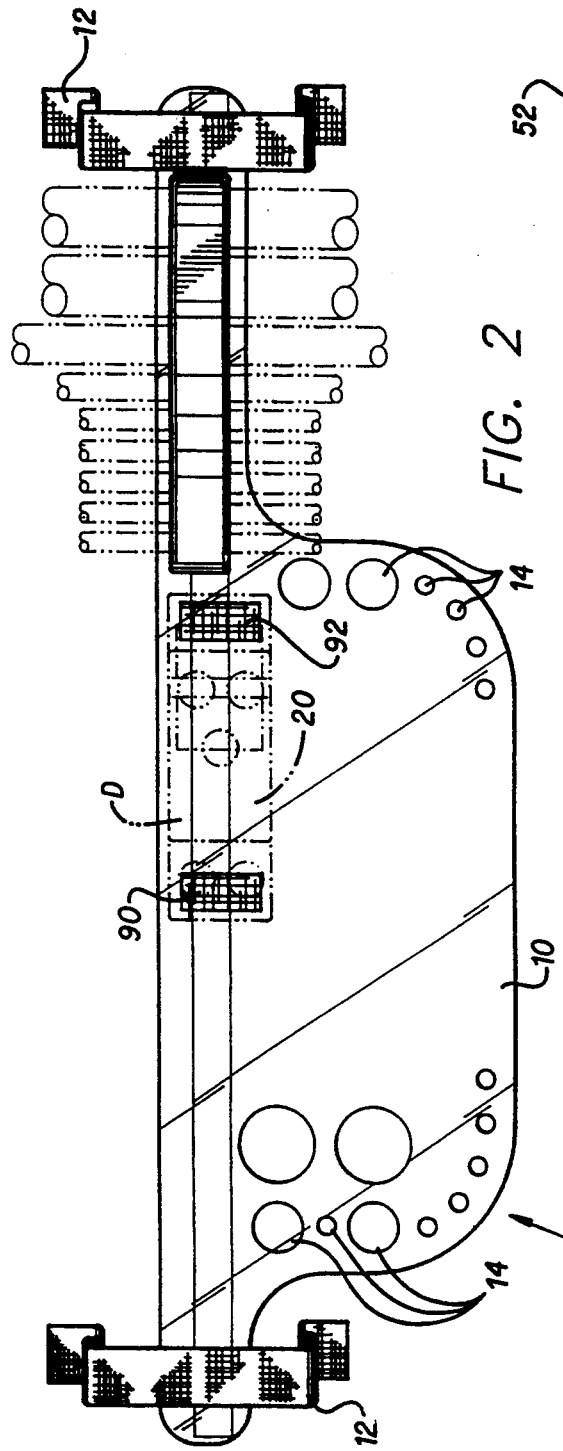
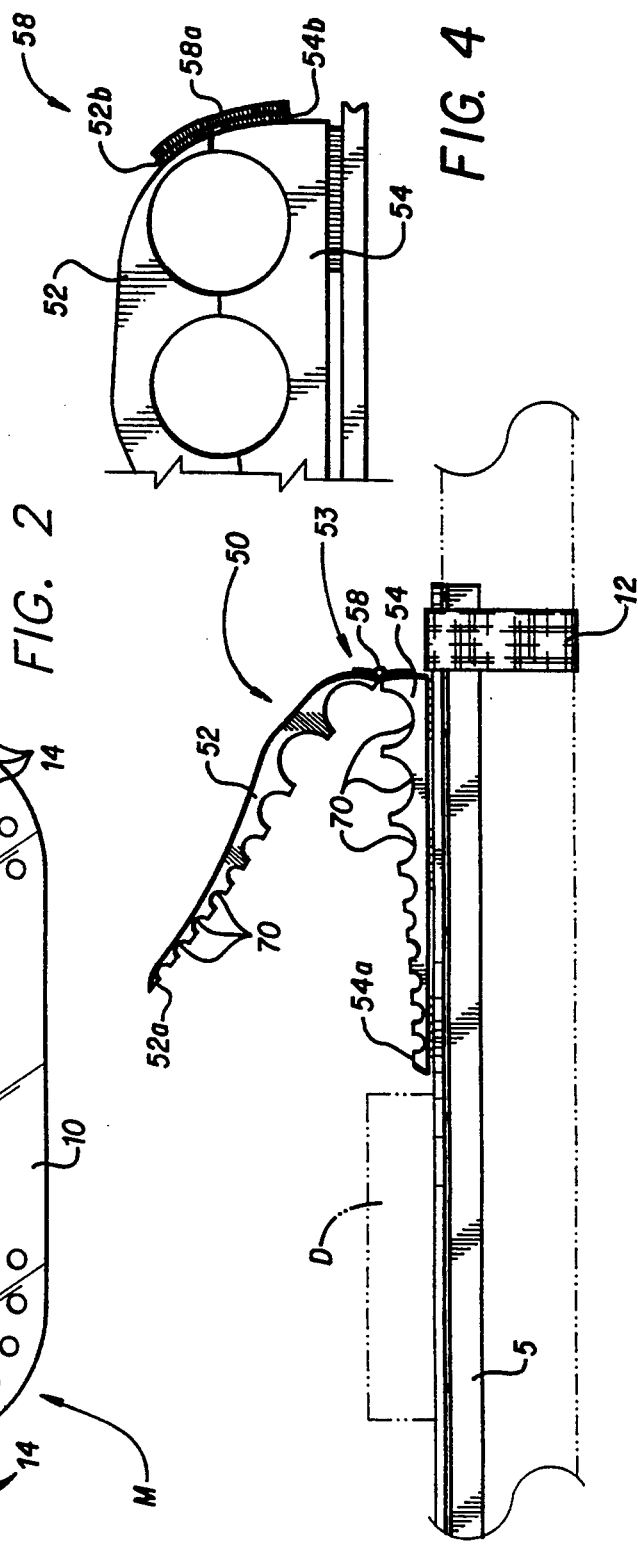

MEDICAL TUBING AND IMPLEMENT ORGANIZER

BACKGROUND OF THE INVENTION

1. Field of the Invention

The present invention relates to tubing and implement organizers. More specifically, it relates to tubing and implement organizers for use in a medical facility. Even more specifically, it relates to a tubing and implement organizer for use in a hospital; one that removably straps to the side rail of a hospital bed and has both a holder and a flat base, which are, additionally, demountably engaged with one another.

2. Description of the Prior Art

In a hospital environment, as medical equipment proliferates, and especially in Intensive Care Units, there exists a need to aid the caregivers in organizing the implements necessary to maintain and/or perform procedures on the patient. There have been a number of patents issued that address the problem, especially patents directed towards the maintenance of various types of tubes in a fixed relationship to the patient.

The first patent in this discussion is U.S. Pat. No. 3,696,920 issued to Charles Arthur Lahay on Oct. 10, 1972. This discloses a device for organizing objects that consists of a block of semi-rigid foam with cylindrical channels passing through it. There are beveled slots connecting the channels to the top surface of the block to allow objects to be inserted and withdrawn from the channels. On the bottom, there is pressure sensitive tape to adhere the device to a location and the entire unit is packed in a strippable, sterile enclosure.

In U.S. Pat. No. 4,417,710 issued to Edwin L. Adair on Nov. 29, 1983 discloses a combined surgical instrument and tube holding device. The device comprises a pad and a tube holding strip. The pad is attached to a fabric layer having a removable cover, a nesting surface, and an attachment strip; the last two being engageable by hook and loop type fasteners.

Another patent that concerns tubing holders in U.S. Pat. No. 4,606,735 issued to Joseph R. Wilder et al. on Aug. 19, 1986. This device consists of a flexible strip with upstanding wings and slotted keyholes to engage the tubing. It is disclosed that pressure sensitive tape is to be attached to the body of the patient and then that the device is fixed in place with an engaging hook and loop type fastener.

In U.S. Pat. No. 4,795,441 issued to Kunjlata M. Bhatt on Jan. 3, 1989 discloses a medication administration system wherein a tray is supported by a first box that has sliding clamps to secure it to a table. The tray has supporting syringes mounted thereon. A second box, held adjacent to the first box by U-shaped clips, can hold supplementary equipment.

Finally, U.S. Pat. No. 5,102,399 issued to Young K. Chu on Apr. 7, 1992 discloses a clinical tube holder. A suction tube holder includes a bore attached to a mounting block. The bottom of the mounting block has a fastening material that can be stuck to a structural support surface.

None of the above inventions and patents, taken either singly or in combination, is seen to describe the instant invention as claimed.

SUMMARY OF THE INVENTION

The present invention is a medical implement and tubing organizer that allows medical implements to be held in a convenient location proximate to a patient and also allows the medical tubes to be organized and ordered according to size. The tubes are held in generally cylindrical lateral bores in the tubing holder. The holder is in detachable engagement with a substantially flat base portion. The base portion has a plurality of apertures adapted to receive and hold medical implements. The flat base portion also has a strap or the like to engage the rail or horizontal strut of a hospital bed. Thus, the entire unit is held in a fixed relationship with the patient for the convenience of the caregiver and the tube holding portion can be removed from the base, if desired, to facilitate turning or relocating the patient.

Accordingly, it is a principal object of the invention to provide a medical implement and tubing organizer where the tube holding portion of the device is demountably attached to the flat base portion.

It is another object of the invention to provide a medical implement and tubing organizer where the base portion of the device is easily attachable and detachable to the side rail of a hospital bed.

It is a further object of the invention to provide a medical implement and tubing organizer where the tubing holder portion is hinged at one end and, at the other, has a releasable closure means to secure the tubes.

It is yet a further object of the invention to provide a medical implement and tubing holder wherein when the tube holding portion of the device is in a closed configuration, the tubes held therein are maintained in a fixed apart relationship.

Still another object of the invention to provide a medical implement and tube organizer where the base portion includes a number of apertures designed to accommodate medical implements and accessories.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 2 is a top view of the medical implement and tubing organizer.

FIG. 3 is a partial side view showing the tube holder portion of the device in an open configuration.

FIG. 4 is a partial side elevational view of an alternative embodiment of a hinge of the medical implement and tubing organizer.

Similar reference characters denote corresponding features consistently throughout the attached drawings.

DETAILED DESCRIPTION OF THE PREFERRED EMBODIMENTS

Figure 1:
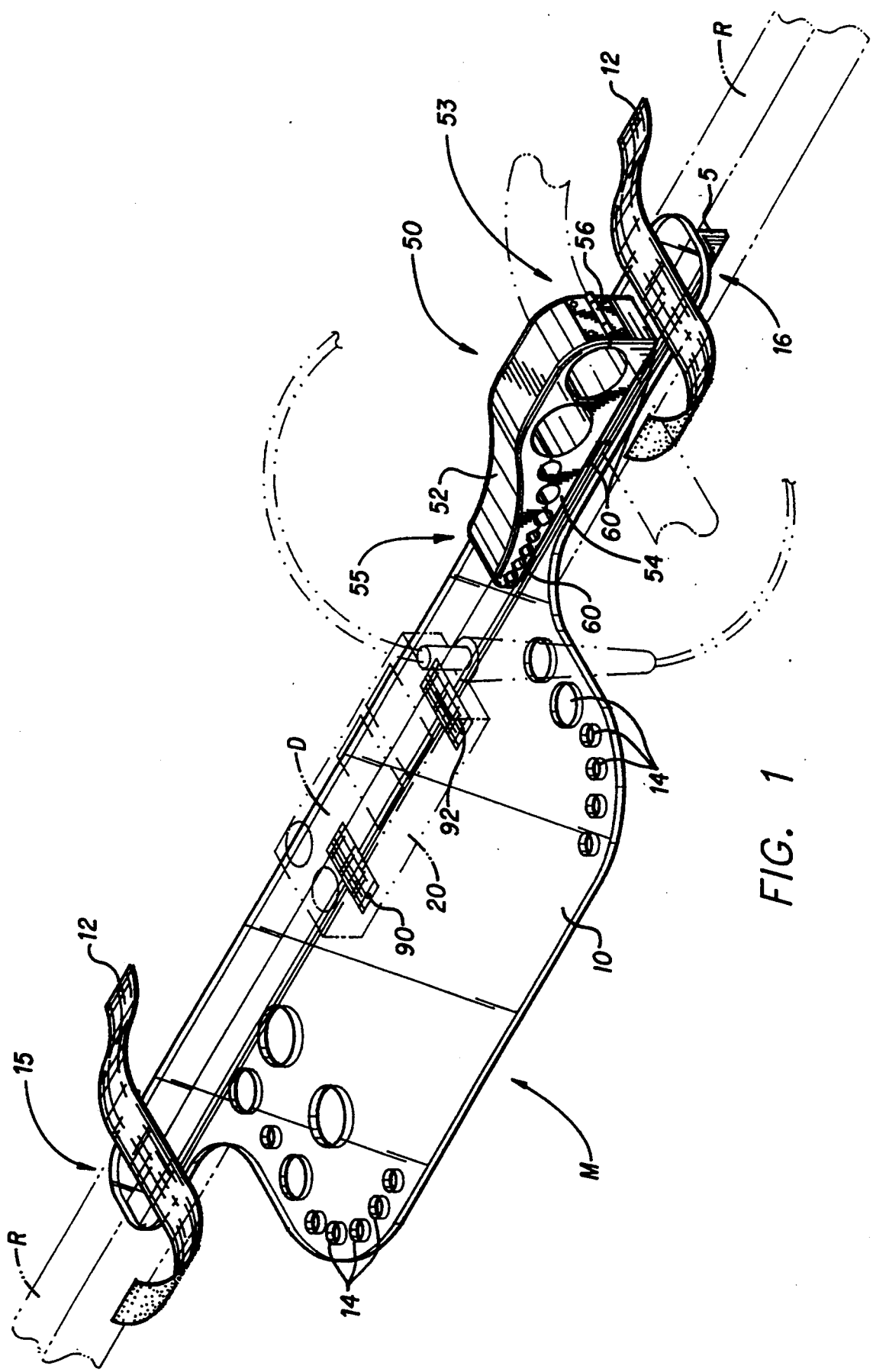
FIG. 1 is an environmental perspective view of the medical implement and tubing organizer.

Referring to FIGS. 1 and 2, the medical implement and tubing holder M is shown. In FIG. 1, the implement and tubing holder M is shown attached to a hospital bed rail R. The implement and tubing holder M has a flat base portion 10 and a tube holder 50. The base portion 10 is, in the preferred embodiment, made of a plastic material and is attached to the hospital bed rail R by two straps, both denoted 12. For added stability, the base portion 10 has an integral protruding ridge 5

(shown in FIGS. 1 and 3) that extends parallel to its longitudinal axis. The attachment points of the straps 12 are proximate the two ends 15, 16 of the base portion 10. The straps are, in the preferred embodiment, of the type well known in the art where the complementing hook and loop fastening materials are located on opposite sides of the strap with the loop or nesting material being on the outer side. Each of the straps could be fastened at one end to the base portion 10 so as to prevent them from being misplaced and ensuring that they are always convenient to the user. Referring to FIG. 2, it is seen that the base portion 10 has a number of apertures 14. The apertures 14 are of different sizes to accommodate a number of different medical implements and accessories such as the small cups for water to aid in taking medication, suction devices, syringes, thermometers, or any number of other objects that the caregiver may wish to keep on hand. It should be noted that the arrangement of the apertures shown in FIGS. 1 and 2 is arbitrary and any arrangement facilitating the efficient use of the device is possible. There is a space 20 provided proximate the middle region of the base portion 10. This space 20 can be provided with an adhesive or other engaging type surface to allow a device D such as a pacemaker or tracheotomy maintenance care kit to be placed on it and fixed thereon. In the preferred embodiment, the base portion 10 has on it one of two mutually engageable surfaces 90, 92, such as a hook and loop type fastener, with the complementing surface being on the pacemaker, tracheotomy maintenance kit, or like sized device D.

Referring especially now to FIGS. 1 and 3, the tube holder 50 is shown. The tube holder has an upper member 52, a lower member 54, a hinge means 56 that defines a pivot point, a releasable closure means 55 made up of mutually engaging hook and loop type fasteners applied to the surfaces 52a and 54a (shown in FIG. 3), and a detachable engagement means 60 (shown in FIG. 1), the last allowing the tube holder 50 to be detached, if desired, from the base portion 10. The detachable engagement means 60 is, in the preferred embodiment, mutually engaging hook and loop type fastening surfaces. The upper member 52 and lower member 54 of the tube holder 50 are, in the preferred embodiment, made of a molded plastic material and generally become thicker vertically towards the hinged end 53 of the tubing holder 50. There are a plurality of mutually complementing cavities 70 in the upper member 52 and lower member 54. These cavities 70 are of a variety of sizes that conform to the practice of having standard diameters for different tubing purposes. When tube holder 50 is in a closed configuration, the cavities 70 form generally cylindrical lateral bores. Examples of the types of tubing that could be held in the lateral bores formed from the complementing cavities 70 are ventilator tubes, nasogastric tubes, IV lines, swan-ganz lines, and central venous lines. The cavities 70 increase in size at intervals by discrete amounts as they approach the hinged end 53 of the tubing holder 50. The hinge means 56 is, in the preferred embodiment, of the well known leaf hinge type, though it should be understood that any number of other types, such as a living hinge could be used. FIG. 4 shows an alternative embodiment of the invention with a living hinge 58. The hinge means 58 may include a spanning strip 58a with a hook or loop type fastening surface 52b located on the top member 52 and bottom member 54 to engage with a complementing surface 54b on the strip. This arrangement allows the top member 52 and bottom member 54 to be completely separated if desired.

In use, therefore, the medical implement and tubing holder M can be quickly attached to the bed rail R by looping the straps 12 about the bed rail R and, for added stability, positioning the base portion 10 so that the ridge 5 abuts the bed rail R. The tube holder 50 is opened by disengaging the hook and loop type fastening surfaces located at 52a and 54a, and rotating the upper member 52 and lower member 54 about the pivot point defined by the hinge means 56, to allow access to the mutually complementing cavities 70. This open configuration is shown in FIG. 3. The various medical tubes are placed in the appropriately sized cavities 70 and upper member 52 and lower member 54 are again rotated by hinge means 56 to bring tubing holder 50 into a closed configuration. Medical implements can be placed into the apertures 14 in the base member 10 as needed. If other hardware, such as a pacemaker or the like is needed, it can be located in the space 20 so as to be conveniently available to the caregiver. If at any point the patient needs to be moved, for example to be turned in bed or taken to another location, the tube holder 50 can be detached from the base portion 10 and manipulated in whatever way necessary to keep the tubes from tangling or kinking.

It is to be understood that the present invention is not limited to the embodiments described above, but encompasses any and all embodiments within the scope of the following claims.

I claim:

1. A medical implement and tubing organizer comprising a base portion for supporting said organizer on a supporting surface and receiving medical implements, and a multiple tubing holder portion for carrying a plurality of tubes;

said base portion including an elongated support element and a substantially planar element defining a plurality of aperture located in said planar element and adapted to receive medical implements;

said multiple tubing holder portion extending out of a plane defined by a surface of said base portion and including:

a top member, a bottom member positioned beneath said top member, hinging means defining a pivot point between said top member and said bottom member, said hinging means is a living hinge, said living hinge is removable from said top member and said bottom member, releasable and reusable closure means for repeatedly holding said top member and said bottom member in a generally parallel relationship and for releasing said top member from said bottom member, said releasable and reusable closure means attached to both said top and bottom members, a plurality of mutually complementing cavities cut out of both said top and bottom members, and removable and reusable engagement means integral to said bottom member for repeatedly attaching said multiple tubing holder portion to said base portion and for releasing said multiple tubing holder portion from said base portion, whereby when said bottom and said top member are rotated about said pivot point and placed in a generally parallel relationship, said mutually complementing cavities define a plurality of generally cylindrical lateral bores in a side-by-side arrangement; wherein said multiple tubing holder portion and said base portion are configured so said multiple tubing holder portion is removable from said base portion, while maintaining medical implements in said base portion and tubing in said multiple tubing holder portion in predetermined orientations, respectively.

2. The medical implement and tubing organizer according to claim 1, wherein said removable engagement means is a hook and loop type fastener.

3. The medical implement and tubing organizer according to claim 1, wherein said closure means is a hook and loop type fastener.

4. The medical implement and tubing organizer according to claim 1, wherein said multiple tubing holder portion is removably attached to said elongated support element of said base portion.

5. The medical implement and tubing organizer according to claim 1, wherein said base portion is configured so a top surface of said elongated support element and a top surface of said substantially planar element define a horizontal plane.

6. The medical implement and tubing organizer according to claim 1, wherein said plurality of apertures in said base portion further comprise a plurality of differently sized apertures.

7. The medical implement and tubing organizer according to claim 1, wherein said plurality of lateral bores further comprise a plurality of differently sized lateral bores.

8. The medical implement and tubing organizer according to claim 1, wherein said base portion and said multiple tubing holder portion are configured so medical implements carried in said base portion define a substantially right angle with tubing carried in said multiple tubing holder portion.

9. The medical implement and tubing organizer according to claim 1, wherein said base portion further includes adjustable engagement means for attaching said base portion to a bed side rail.

10. The medical implement and tubing holder according to claim 9, wherein said adjustable engagement means comprises a strap having hook and loop type engaging elements.

11. The medical implement and tubing organizer according to claim 1, wherein said base portion further includes a protruding rib parallel to a longitudinal axis of said base portion.

12. The medical implement and tubing organizer according to claim 11, wherein said base portion is configured so a top surface of said elongated support element and a top surface of said substantially planar element define a horizontal plane.

13. The medical implement and tubing organizer according to claim 12 wherein said plurality of apertures in said base portion further comprise a plurality of differently sized apertures.

14. The medical implement and tubing organizer according to claim 13, wherein said plurality of lateral bores further comprise a plurality of differently sized lateral bores.

* * * * *